United States Patent [19]

Duthoy

[11] Patent Number: 4,625,726
[45] Date of Patent: Dec. 2, 1986

[54] KIDNEY STONE RETRIEVER
[76] Inventor: Everette J. Duthoy, 1472 Cherry Hill Rd., St. Paul, Minn. 55118
[21] Appl. No.: 638,381
[22] Filed: Aug. 7, 1984
[51] Int. Cl.$^4$ ............................................. A61B 17/00
[52] U.S. Cl. ................................................... 128/328
[58] Field of Search ...................... 128/328, 356, 345
[56] References Cited

U.S. PATENT DOCUMENTS 1,677,671  7/1928  Councill .............................. 128/328

OTHER PUBLICATIONS

Article, "Balloon-Dilatation of Lower Ureter to Facilitate Cystoscopic Extraction of Large Ureteral Calculi", by Alvin B. Rutner, Mar. 1983.
Brochure, "Pfister-Schwartz Stone Retriever", by V. Mueller, V. Mueller del Caribe Inc., Building 1132, Borinquen Airport, Aguadilla, Puerto Rico 00604, Mar. 1982.

Primary Examiner—Robert Peshock

[57] ABSTRACT

The present invention is directed to a kidney stone retrieval device which includes a basket between a ferrule and a tube. Both the tube and the ferrule have aligned passages for receiving a guide wire. In this way, the guide wire may be inserted into a ureter past the stone so that the retrieval device may be pushed along the guide wire until the basket reaches and passes the stone, whereupon the device is maneuvered for dislodging and retrieving the stone with the basket.

3 Claims, 10 Drawing Figures

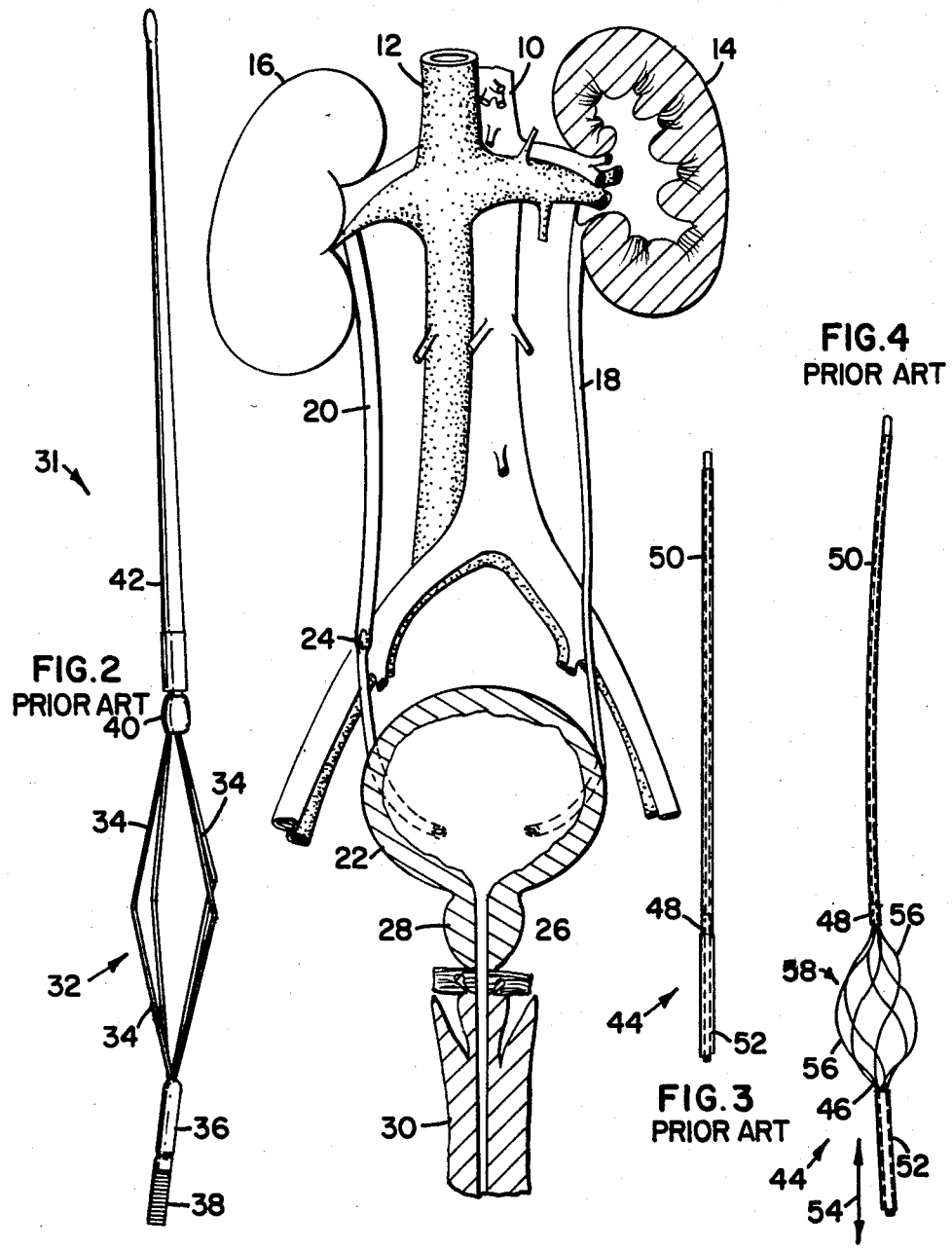

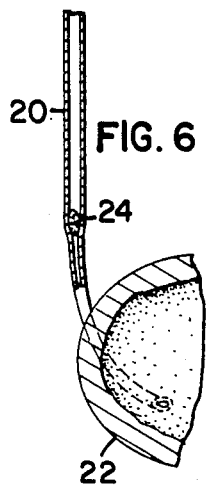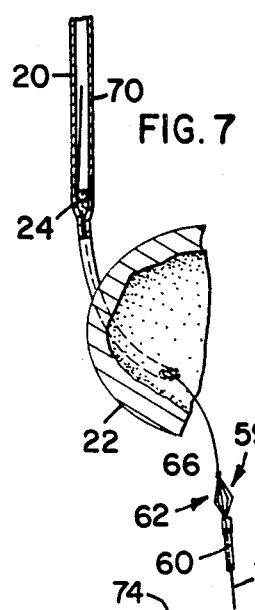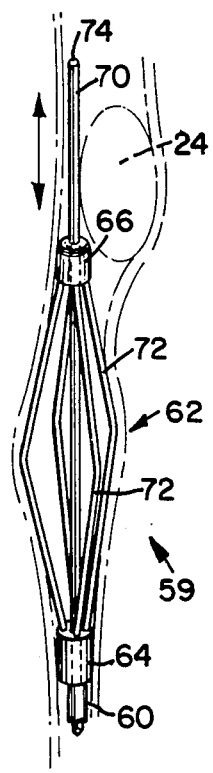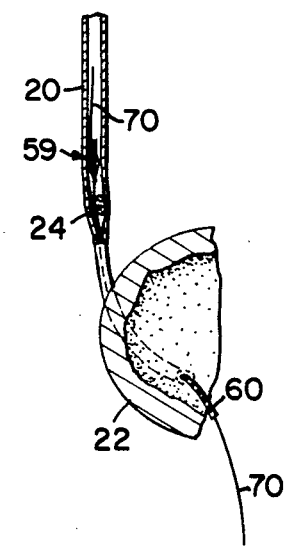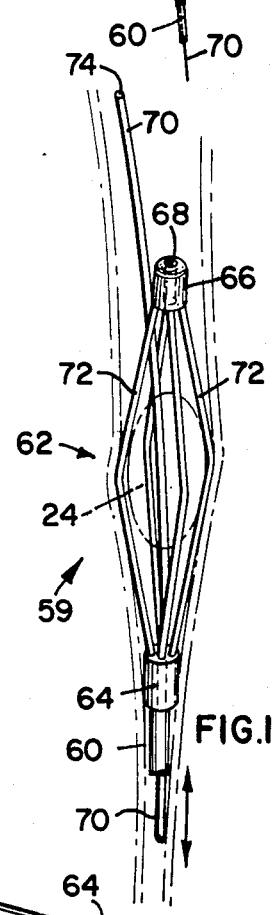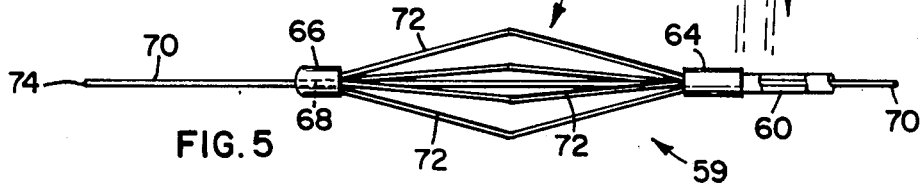

KIDNEY STONE RETRIEVER

FIELD OF THE INVENTION

The present invention is directed to the general field of urology and, more particularly, to a device for dislodging and capturing a stone from a person's ureter.

BACKGROUND OF THE INVENTION

Waste body fluids flow from the kidney through the ureter to the bladder. The fluids pass from the bladder through the urethra to exit a person's body. A blockage occasionally forms in the ureter of some people. The blockage is usually comprised of a hard stone-like material called calculus. Such a blockage can be painful and dangerous since it restricts the flow of waste fluids through the ureter. Ureteral calculus, more commonly known as a kidney stone, may be removed surgically. It is preferable, however, to try to capture the stone and pull it through the ureter, baldder and urethra. Devices and procedures for such capture and removal are, thus, known.

The most common stone retriever device is made from a cable having a wire basket at one end of the cable with a relatively short, somewhat flexible, rod-like end member, called a filiform, at the end of the basket opposite the cable. The basket is usually made of four equally spaced-apart wires which are sufficiently rigid to hold a large V-shape. The filiform of the device is inserted into the ureter and worked past the stone. As the basket is maneuvered alongside the stone, the stone moves into the space surrounded by the wires and is hopefully captured for removal on removal of the cable and basket. The problem with this device is that it is extremely difficult to work the basket around or even with the stone in order to capture the stone. Consequently, the removal procedure may be time consuming and is prone to failure.

Another known device includes a six wire cable having a filiform at the end. The cable is received in a tube. A handle moves the tube about one inch in either direction along the cable. When the tube is retracted, a portion of the cable is exposed, and the wires are preformed and yieldably flexible to expand into a basket shape. This device is used similarly to the previously described device, except the basket is enclosed in the tube and, therefore, is easily moved past the stone once the filiform is worked past the stone. The problem with this device, however, is that the wires of the cable are necessarily thin and flexible and, consequently, when the basket is pulled back past the stone, the wires too often simply collapse and do not capture or dislodge the stone.

Consequently, present stone retrievers are successful in some cases and not successful in far too many. Widespread use of this type of procedure, therefore, probably depends upon the identification of an improved surgical tool.

SUMMARY OF THE INVENTION

The present invention is directed to a device for removing a stone from a ureter comprising a hollow cable, a mechanism for retrieving the stone wherein the retrieving mechanism has an end button with an opening in it, and a guide wire for passing through the hollow cable and selectively through the opening in the end button of the retrieving mechanism. In a preferred form, the retrieving mechanism is a basket made of a plurality of wires spaced about and spaced outwardly from the imaginary extension of the centerline of the hollow cable.

The device is used by inserting the guide wire into a ureter and past a stone lodged in the ureter. The hollow cable, basket and end button are then threaded onto the guide wire and slid over the guide wire until the basket moves past the stone. The guide wire is then either pulled from the end button and cable or is simply pulled from the end button and extended again past the end button without going through the opening in the end button. With the latter procedure, the guide wire moves substantially to the side of the basket so as not to be in the way of capturing the stone, but remains in place so that if the basket does not capture the stone on a first pass back past the stone, the guide wire is still in place so that the end button, basket and cable may be rethreaded onto the guide wire and reinserted along it for another try.

To make it easier to move the basket past the stone during the insertion movement, it is possible to insert a catheter into the ureter up to the stone. The guide wire is passed through the catheter and past the stone. The catheter may then also be worked along the guide wire past the stone. The end button, basket and cable may then be slid over the guide wire, but within the catheter such that the basket is compressed by the walls of the catheter, until the basket passes past the stone at which point it expands and is ready to be retracted in order to capture the stone. The catheter is then retracted before moving the guide wire out of the center of the basket and retracting the basket.

The present device solves the problems of the art, since it is easily and repeatedly passed by the stone on an insertion stroke for positioning prior to retraction. In addition, a sufficiently strong basket may be used to minimize compression of the basket by the stone during retrieval.

These advantages and other objects obtained by the present invention are further explained and may be better understood by reference to the preferred embodiment shown in the drawings and described in detail thereafter.

BRIEF DESCRIPTION OF THE DRAWINGS

FIG. 1 is a front illustration, partially in cross section, of several body parts and shows a piece of calculus in the ureter on the left;

FIG. 2 is a view in elevation of a first prior art device;

FIG. 3 is a view in elevation of a second prior art device wherein the basket is contained in a tube;

FIG. 4 is a view in elevation of the device of FIG. 3 wherein the basket is expanded;

FIG. 5 is an elevational view in partial cross-section of a device in accordance with the present invention;

FIG. 6 is a detail view of portions of a bladder and ureter with a stone in the ureter;

FIG. 7 is an illustration showing a guide wire located in the ureter and past the stone;

FIG. 8 is a view in elevation of a device in accordance with the present invention, showing a ureter and stone in phantom;

FIG. 9 is an illustration showing the present invention with the basket past the stone in the ureter; and FIG. 10 is a view in elevation of a device in accordance with the present invention showing the guide wire to one side of the end button and showing in phantom the ureter and captured stone.

DETAILED DESCRIPTION OF THE PREFERRED EMBODIMENT

Before describing the preferred embodiment of the invention, it is appropriate to provide a frame of reference by discussing certain body parts. Furthermore, it is appropriate to describe in more detail prior art devices discussed hereinbefore so as to clearly distinguish the art from the present invention. Referring then to the drawings, like reference numerals are used to designate identical or corresponding parts throughout the several views.

With reference to FIG. 1, several parts of a male anatomy are shown. The aorta 10 and vena cava 12 are provided for reference. Kidneys 14 and 16 are shown on opposite sides of the aorta 10 and vena cava 12. Ureters 18 and 20 lead from kidneys 14 and 16, respectively, to bladder 22. A piece of calculus or stone 24 is shown in ureter 20. Urethra 26 extends from bladder 22 through prostrate 28 and penis 30. Female body parts are similar for purposes of the present invention except the urethra passes more directly to an external orifice.

With respect to FIG. 2, the illustrated prior art device 31 shows a basket 32 comprised of four wires 34, each being semi-rigid and having a large V-shape. Basket 32 is attached at a first end with connector 36 to cable 38 and at a second end, opposite the first end, with connector 40 to filiform 42. As indicated hereinbefore, device 31 is used by working filiform 42 into a ureter, such as 20, and past a stone 24. The problem with device 31 is that it is difficult to work basket 32 past stone 24 and, once that is accomplished, the difficult threading of filiform 42 and basket 32 past stone 24 must be done again and again with evermore risk to the patient if stone 24 is not easily dislodged and captured by basket 32 on a first retraction of device 31.

A second prior art device 44 is shown in FIGS. 3 and 4. Device 44 includes a cable 46 attached at an end 48 to a filiform 50. Cable 46 is received in a tube 52 which is slidable along cable 46 as indicated by arrow 54. Cable 46 is made of a plurality of wire strands 56. The strands are formed in the region of basket 58 to spring outwardly when tube 52 is retracted from end 48. As shown in FIG. 3, when tube 52 is pushed toward end 48, strands 56 are compressed together and enclosed within tube 52. In use, basket 58 is enclosed in tube 52 as shown in FIG. 3 during insertion of device 44 through the various passages including ureter 24 until filiform 50 is worked past a stone such as the stone shown at numeral 24. When the complete filiform 50 and a portion of tube 52 is past stone 24, tube 52 is slid in a retraction direction to allow basket 58 to expand. Device 44 is then partially retracted to try to dislodge and capture stone 24 in basket 58. The problem with device 44 is that wires 56 must be sufficiently flexible to be compressed by tube 52 as tube 52 moves longitudinally along cable 46. Such flexible wires are often simply deflected by a stone 24 rather than functioning to dislodge and capture stone 24.

The preferred embodiment of the present inventive device 59 is shown in FIG. 5 and includes a hollow tube 60 with a basket 62 attached at its distal end with a connector 64. The second end of basket 62 is attached to ferrule or end button 66. Ferrule 66 has a central passage 68 which is substantially aligned with an extension of the centerline of tube 60. A guide in the form of wire 70 is slidable through tube 60, connector 64, basket 62 and ferrule 66. When completely inserted, guide wire 70 extends from the proximal end of tube 60 through and beyond ferrule 66. Basket 62 is preferably comprised of four semi-rigid wires 72 formed in a large V with the opposite ends of each wire 72 attached to connector 64 and ferrule 66.

The use of device 62 is illustrated in FIGS. 5-10. A portion of bladder 22 and ureter 20 with a stone 24 is shown in FIG. 6. Device 59 is shown in FIG. 7 with guide wire 70 threaded through tube 60, basket 62 and ferrule 66, as well as into ureter 20 to a location past stone 24. In FIG. 8, basket 62 is approaching stone 24. In FIG. 9 basket 62 is shown as having passed stone 24. Since the purpose of the operation is to remove stone 24, however, it may not be necessary to move basket 62 completely past stone 24 to dislodge and capture stone 24 in basket 62. In order to capture stone 24, however, it is usually necessary to at least retract guide wire 70 either from extending through basket 62 or from extending through ferrule 66 as shown in FIG. 10. There is advantage to retracting guide wire 70 only sufficiently far so that its tip 74 comes free of ferrule 66 and into basket 62. Then, guide wire 70 may be pushed in the insertion direction. Generally, guide wire 70 will not rethread itself into ferrule 66. In an alternate embodiment, ferrule 66 may have a conically shaped end to deflect guide wire 70. By missing opening 68, guide wire 70 is deflected sidewardly so that it no longer extends through the center of basket 62. In this configuration, basket 62 is much better able to dislodge and capture stone 24. Furthermore, if basket 62 is pulled in a retraction direction past stone 24 without capturing stone 24, device 59 may be pulled from the patient without removing guide wire 70 so that device 59 may be rethreaded onto guide wire 70 and the procedure repeated. In this way, the most difficult portion of the procedure, namely threading guide wire 70 into urether 20 and past stone 24 need not be redone.

It is further understood that device 59 may be used in conjunction with a catheter (not shown). In such a procedure the catheter is first inserted into the ureter up to stone 24. Device 59 including guide wire 70 is then inserted into the catheter. Guide wire 70 is pushed out the end of the catheter and worked past stone 24 as indicated hereinbefore. In some cases, it may be possible to work the catheter past a portion of or all of stone 24. If that is possible, basket 62 is then easily pushed through the catheter and into ureter 20 above stone 24. The catheter is then pulled away from stone 24 and the stone is dislodged and retrieved as discussed hereinbefore.

The present invention solves the problems of the prior art in that device 59 is easily pushed along guide wire 70 for repeated attempts at dislodging and removing a stone 24 if repeated attempts are necessary. Furthermore, in situations where it is difficult to move a basket alongside or past a stone, device 59 may be used in conjunction with a catheter. This latter procedure, of course, retains the advantages of using the guide wire, also. Furthermore, device 59 can use a basket of sufficiently stiff wire so that there is truly a good chance of dislodging and capturing stone 24, as opposed to prior art devices which have flexible wire baskets which often collapse.

It should be noted too that a device in accordance with the present invention is applicable for use either transurethrally from below through the penis or female urethra as discussed hereinbefore or percutaneously via the kidney for stones located in the upper ureter.

Even though the preferred embodiment of the present invention has been described in detail, including advantages and details of structure and function, it is understood that the disclosure is only representative of the concept. Consequently, changes made, especially in matters of shape, size and arrangement, to the full extent extended by the general meaning of the terms in which the appended claims are expressed, are within the principle of the invention.

What is claimed is:

1. A device for removing a stone from a ureter, comprising:
   a hollow tube having proximal and distal ends,
   means having proximal and distal ends for retrieving said stone, said retrieving means having a ferrule with an opening therein at its distal end, said ferrule opening being in substantial alignment with said hollow tube and extending through the ferrule;
   means for attaching said retrieving means to the proximal end of said tube and having an opening extending therethrough that opens to the retrieving means and to the hollow tube; and
   a guide wire for slidably passing through said hollow tube, the attaching means opening and selectively through the opening in said ferrule of said retrieving means;
   whereby said guide wire may be inserted in said ureter past stone and said ferrule, said retrieving means and said tube may slid over and along said guide wire until said retrieving means moves to the vicinity of said stone, and said guide wire being moveable from alignment between said tube and the opening in said ferrule thereby allowing said retrieving means to be moved in said ureter to capture said stone and remove said stone.

2. A device for removing a stone from a ureter, comprising:
   a hollow tube having a proximal end, a distal end and a centerline from its proximal end to its distal end;
   a basket for capturing a kidney stone and having a proximal end, a distal end and a plurality of wires space about and spaced outwardly from an imaginary extension of the centerline of said hollow tube;
   means for attaching the distal end of said basket to the proximal end of said hollow tube and having an opening that opens to the hollow tube and into the basket;
   a ferrule joined to the proximal end of said basket, said ferrule having an opening extending therethrough that is substantially aligned with the centerline extension of said hollow tube and opens into said basket;
   a guide wire for slidably passing through said hollow tube, the attaching means opening, the basket and the opening in said ferrule and being retractable through the ferrule opening and then extendable between the basket wires to extend outwardly of the basket;
   whereby said guide wire may be inserted in said ureter past said stone and then said ferrule, basket and tube slid over said guide wire until said basket passes the stone, said guide wire being moveable from alignment with the centerline extension so said basket may be moved to capture said stone and remove said stone while the guide wire remains extended into the ureter.

3. A method for removing a stone from a ureter, comprising the steps of:
   inserting a guide into a ureter and past a stone lodged in the ureter;
   sliding a hollow cable and a ferrule with a basket therebetween over said guide to a location that the basket is adjacent to said stone said ferrule having an opening therein through which said guide extends as the basket is moved adjacent to the stone;
   moving said guide from passing through the opening in said ferrule; and
   pulling said cable so as to capture said stone in said basket to remove said stone from said ureter.

* * * * *